United States Patent
Cacchiotti et al.

(10) Patent No.: US 7,070,410 B2
(45) Date of Patent: Jul. 4, 2006

(54) ORTHODONTIC DEVICE FOR ATTACHMENT TO ORTHODONTIC WIRE

(76) Inventors: Dino A. Cacchiotti, 791 N. Westshore Dr., Moses Lake, WA (US) 98837; Lawrence F. Cacchiotti, 3011 Marks Rd., Yakima, WA (US) 98908

( * ) Notice: Subject to any disclaimer, the term of this patent is extended or adjusted under 35 U.S.C. 154(b) by 47 days.

(21) Appl. No.: 10/933,617

(22) Filed: Sep. 2, 2004

(65) Prior Publication Data

US 2006/0046225 A1    Mar. 2, 2006

(51) Int. Cl.
*A61C 3/00* (2006.01)
(52) U.S. Cl. .......................................... 433/19; 433/18
(58) Field of Classification Search ............. 433/18–24
See application file for complete search history.

(56) References Cited

U.S. PATENT DOCUMENTS

| | | | | | |
|---|---|---|---|---|---|
| 3,618,214 | A | * | 11/1971 | Armstrong ................... | 433/19 |
| 3,793,730 | A | * | 2/1974 | Begg et al. ................... | 433/14 |
| 3,893,241 | A | * | 7/1975 | Moriarty ....................... | 433/22 |
| 4,330,271 | A | * | 5/1982 | Anderson ...................... | 433/3 |
| 4,424,031 | A | * | 1/1984 | Dahan ......................... | 433/18 |
| 4,424,033 | A | * | 1/1984 | Wool ........................... | 433/20 |
| 4,462,800 | A | * | 7/1984 | Jones .......................... | 433/19 |
| 4,551,095 | A | * | 11/1985 | Mason ......................... | 433/19 |
| 4,708,646 | A | * | 11/1987 | Jasper ......................... | 433/19 |
| 4,795,342 | A | * | 1/1989 | Jones .......................... | 433/19 |
| 4,797,095 | A | * | 1/1989 | Armstrong et al. ........... | 433/22 |
| 5,120,218 | A | * | 6/1992 | Hanson ........................ | 433/19 |
| 5,145,364 | A | * | 9/1992 | Martz et al. .................. | 433/6 |
| 5,183,388 | A | * | 2/1993 | Kumar ......................... | 433/19 |
| 5,352,116 | A | * | 10/1994 | West ........................... | 433/19 |
| 5,435,721 | A | * | 7/1995 | Vogt ............................ | 433/19 |
| 5,505,616 | A | * | 4/1996 | Harwell ....................... | 433/21 |
| 5,540,586 | A | * | 7/1996 | Hanson ........................ | 433/22 |
| 5,545,037 | A | * | 8/1996 | Takeshi ........................ | 433/21 |
| 5,562,445 | A | * | 10/1996 | DeVincenzo et al. ......... | 433/19 |
| 5,645,423 | A | * | 7/1997 | Collins, Jr. ................... | 433/21 |
| 5,645,424 | A | * | 7/1997 | Collins, Jr. ................... | 433/18 |
| 5,651,672 | A | * | 7/1997 | Cleary et al. ................. | 433/19 |
| 5,697,782 | A | * | 12/1997 | Klapper et al. ............... | 433/19 |
| 5,711,667 | A | * | 1/1998 | Vogt ............................ | 433/19 |
| 5,718,576 | A | * | 2/1998 | Schnaitter et al. ............ | 433/22 |
| 5,738,514 | A | | 4/1998 | DeVincenzo et al. | |
| 5,788,486 | A | * | 8/1998 | Klapper et al. ............... | 433/19 |
| 5,846,074 | A | * | 12/1998 | Klapper ....................... | 433/19 |
| 5,879,157 | A | * | 3/1999 | Scheu .......................... | 433/19 |
| 5,897,313 | A | * | 4/1999 | Cleary et al. ................. | 433/19 |
| 5,964,588 | A | * | 10/1999 | Cleary ......................... | 433/19 |

(Continued)

*Primary Examiner*—Cary E. O'Connor
*Assistant Examiner*—Patrick J. Kilkenny
(74) *Attorney, Agent, or Firm*—Michael J. Donohue; Davis Wright Tremaine LLP

(57) ABSTRACT

An orthodontic device allows direct attachment to orthodontic wires. A force module central portion is coupled to upper and lower end caps. The end caps have clip members that permit direct clipping onto the orthodontic wires to thereby retain the force module on the orthodontic wires. The clip members comprise first and second spaced apart curved members curving in a first direction and an intermediate curved member curving in the opposite direction. One or more of the curved members may flex to allow passage of the orthodontic wire. Alternatively the curved members have different radii of curvature to form a gap that is slightly smaller than the expected size of the orthodontic wire to permit the orthodontic wire to be forced between the gap and retained within a receiver portion formed by the curved members.

41 Claims, 18 Drawing Sheets

U.S. PATENT DOCUMENTS

| | | | |
|---|---|---|---|
| 6,053,730 A * | 4/2000 | Cleary | 433/19 |
| 6,113,390 A * | 9/2000 | Sirney et al. | 433/19 |
| 6,120,289 A * | 9/2000 | Cleary et al. | 433/22 |
| 6,162,051 A * | 12/2000 | Brehm et al. | 433/19 |
| 6,168,430 B1 * | 1/2001 | Higgins | 433/19 |
| 6,217,323 B1 * | 4/2001 | Liou | 433/18 |
| 6,234,791 B1 * | 5/2001 | Cleary et al. | 433/18 |
| 6,322,357 B1 * | 11/2001 | Vogt | 433/19 |
| 6,328,562 B1 * | 12/2001 | Sirney et al. | 433/19 |
| 6,354,834 B1 * | 3/2002 | Kanomi et al. | 433/18 |
| 6,358,046 B1 * | 3/2002 | Brehm et al. | 433/19 |
| 6,402,510 B1 * | 6/2002 | Williams | 433/19 |
| 6,413,082 B1 * | 7/2002 | Binder | 433/19 |
| 6,488,498 B1 * | 12/2002 | Mariani, Jr. | 433/11 |
| 6,520,772 B1 * | 2/2003 | Williams | 433/7 |
| 6,547,560 B1 * | 4/2003 | Vazquez | 433/19 |
| 6,558,160 B1 * | 5/2003 | Schnaitter et al. | 433/19 |
| 6,589,051 B1 * | 7/2003 | Cleary | 433/19 |
| 6,669,474 B1 * | 12/2003 | Vogt | 433/19 |
| 6,877,982 B1 * | 4/2005 | Williams | 433/19 |
| 6,884,067 B1 * | 4/2005 | Tuneberg | 433/19 |
| 6,913,460 B1 * | 7/2005 | Cleary et al. | 433/19 |
| 6,935,858 B1 * | 8/2005 | Cleary | 433/18 |
| 2002/0132207 A1 * | 9/2002 | Tuneberg | 433/19 |
| 2002/0164555 A1 * | 11/2002 | Vogt | 433/19 |
| 2003/0022124 A1 * | 1/2003 | Schnaitter et al. | 433/19 |
| 2003/0022125 A1 * | 1/2003 | Cleary | 433/19 |
| 2003/0104335 A1 * | 6/2003 | Chung | 433/18 |
| 2003/0157455 A1 * | 8/2003 | Teramoto | 433/18 |
| 2003/0232301 A1 * | 12/2003 | Cleary et al. | 433/19 |
| 2004/0053188 A1 * | 3/2004 | Callabe et al. | 433/19 |
| 2004/0081937 A1 * | 4/2004 | Graham | 433/19 |
| 2004/0096798 A1 * | 5/2004 | Cleary | 433/18 |
| 2004/0157187 A1 * | 8/2004 | Lin | 433/18 |

* cited by examiner

ORTHODONTIC DEVICE FOR ATTACHMENT TO ORTHODONTIC WIRE

BACKGROUND OF THE INVENTION

1. Field of the Invention

The present invention is directed generally to orthodontics and, more particularly, to an orthodontic device for attachment to orthodontic wires.

2. Description of the Related Art

The use of orthodontic devices, such as braces, is well known in the art. In the past, orthodontic devices required a significant number of metal components wrapped around individual teeth and wire interconnecting the various attachments. This approach was expensive and cumbersome as well as aesthetically unappealing.

With the introduction of powerful adhesives, braces can be implemented with brackets and wire. The brackets can be bonded directly to the surface of individual teeth. The brackets are coupled together with guide wires, often referred to as arch wires. This less obtrusive approach permits the replacement of individual brackets that have broken or become dislodged. In addition, the brackets, elastic modules and arch wire are available in a variety of colors that permit orthodontic devices to become a fashion statement.

In certain circumstances, the orthodontist prescribes that the patient wear "elastics" or "rubber bands" to interconnect the upper and lower braces. Although rubber bands are relatively inexpensive, they are prone to breakage. In addition, patients often remove the rubber bands due to discomfort and thus retard the therapeutic program.

One alternative to rubber bands are orthodontic appliances that resemble heavy coil springs and, in some cases, telescoping metal parts that are wired to adapters on the braces. These appliances cannot be removed by the patient, however, they are also prone to breakage. In addition, they are expensive, large and cumbersome. Furthermore, the metal components in these appliances may cause discomfort and injury to the cheeks of the patient. Accordingly, it can be appreciated that there is a significant need for an orthodontic device that can be readily installed, but which cannot be readily removed by the patient. The present invention provides this and other advantages as will be apparent from the following detailed description and accompanying figures.

BRIEF SUMMARY OF THE INVENTION

In an exemplary embodiment, an orthodontic device is provided to clip an orthodontic force module onto an orthodontic wire and comprises a cap portion having an aperture size to receive and retain the orthodontic force module. A clip member extending from the cap portion clips directly onto the orthodontic wire wherein the orthodontic force module is retained in position by the clip member clipped onto the orthodontic wire.

In one embodiment, the clip member comprises first and second members extending from the cap portion with the first and second members each having a first end portion coupled to the cap portion and a second free end portion. In one embodiment, the free end portion of the first member and the second member are opposing. The device may also comprise a third member extending from the cap portion with the first end portion coupled to the cap portion and a second free end portion with the third member being spaced apart from the first member with the second member intermediate the first and third members.

In one embodiment, the clip member comprises first and second curved members extending from the cap portion with the first curved member having a first radius of curvature and the second curved member having a second radius of curvature different from the first radius of curvature. In one embodiment, the first radius of curvature is greater than the second radius of curvature. Alternatively, the first radius of curvature can be less than the second radius of curvature. In one embodiment, the curved members are flexible and can be forced apart when the clip member is placed over the orthodontic wire. In an alternative embodiment, the first radius of curvature is sufficiently different from the second radius of curvature to form a gap between the free end portion of the first curved member and the free end portion of the second curved member. In an exemplary embodiment, the gap between the free end portions of the first and second curved members is approximately the size of the orthodontic wire.

BRIEF DESCRIPTION OF THE DRAWING(S)

DETAILED DESCRIPTION OF THE INVENTION

As will be discussed in greater detail herein, an orthodontic device disclosed herein can be easily clipped onto orthodontic wire such that the orthodontic device is retained on and fully supported by the orthodontic wire. As will be described in greater detail below, the device is easy to attach to the orthodontic wire but cannot be easily removed by the patient. However, the orthodontist can easily remove and replace the orthodontic device if necessary.

Figure 1:
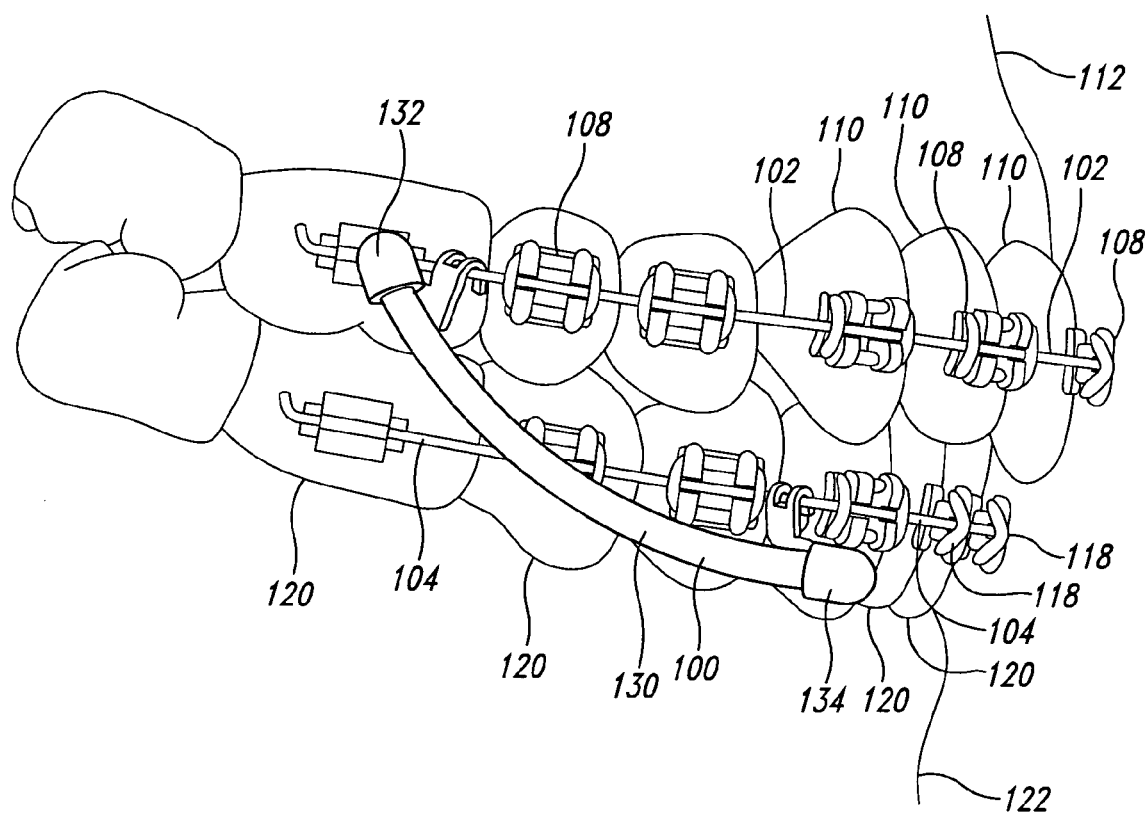
FIG. 1 is a right side view of teeth with the application of braces in one embodiment of the orthodontic device described herein.

FIG. 1 illustrates the placement of an orthodontic device 100 onto orthodontic wire 102 and orthodontic wire 104. As illustrated in FIG. 1, brackets 108 are bonded directly to teeth 110 on an upper dental arch 112 of the patient. Similarly, brackets 118 are bonded directly to teeth 120 of a lower dental arch 122 of the patient. The brackets 118 on the upper arch 112 are coupled together by orthodontic wire 102, sometimes referred to as arch wire. The arch wire 102 extends through slots in each of the brackets 108. Similarly, the arch wire 104 extends through slots in the brackets 118 on the lower arch 122. Tension on the arch wires 102 and 104 may be adjusted to achieve the desired therapeutic effect.

As illustrated in FIG. 1, the orthodontic device 100 is provided in the form of a spring or force module. The primary mode of operation of the orthodontic device 100, when attached, is to provide forward pressure on the lower teeth 120 and backward pressure on the upper teeth 110. This action promotes the correction of the majority of malocclusions typically observed by orthodontists. These are sometimes referred to as "class 2" malocclusions. In addition, the orthodontic device 100 may be suitable for occlusions with increased overbite, which is a condition wherein the upper teeth 110 project farther out from the face than the lower teeth 120.

In an exemplary embodiment, the orthodontic device 100 contains no metal parts. In addition to lower cost, the lack of metal parts reduces risk of injury to the cheeks of the patient that sometimes accompany metal components. As illustrated in FIG. 1, the orthodontic device 100 clips directly onto the upper arch wire 102 at the top end of the orthodontic device and clips directly onto the lower arch wire 104 at the bottom end of the orthodontic device. This may also be seen in the frontal view of the patient's teeth provided in FIGS. 2A and 2B.

Figure 2A:
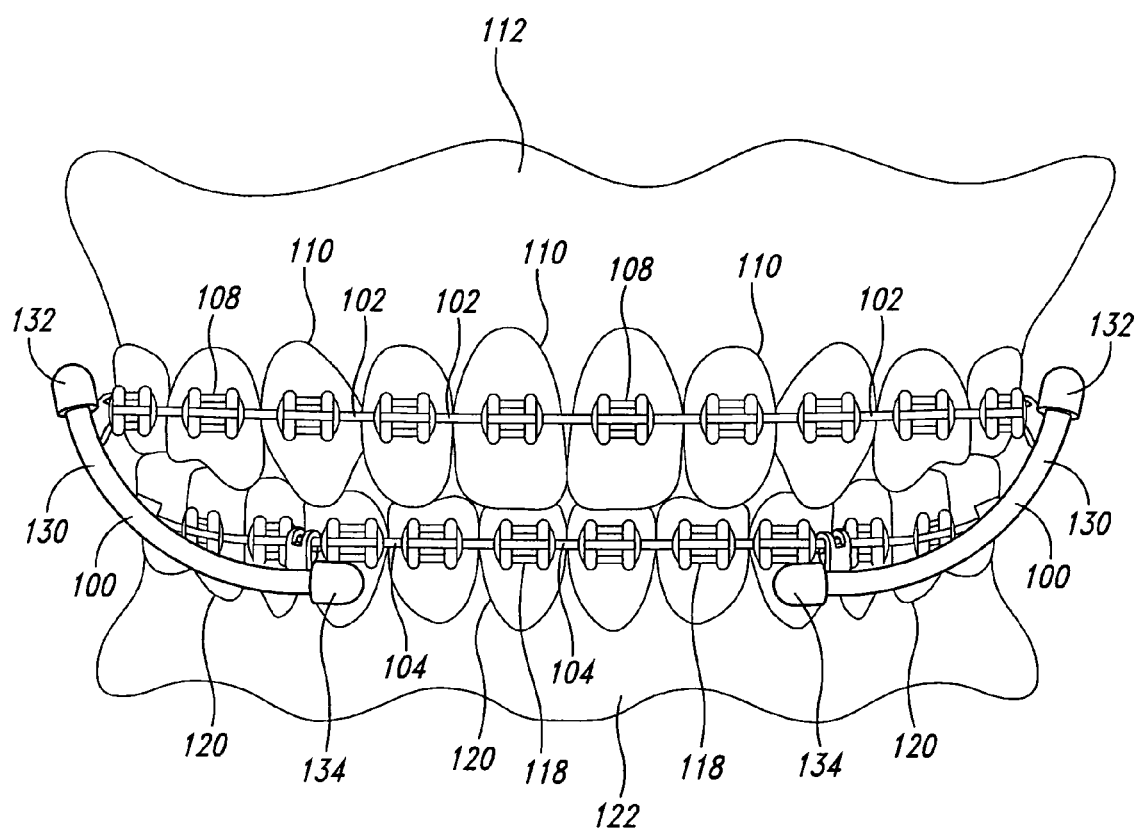
FIGS. 2A and 2B are front views of teeth and braces with the orthodontic device of FIG. 1.
Figure 2B:
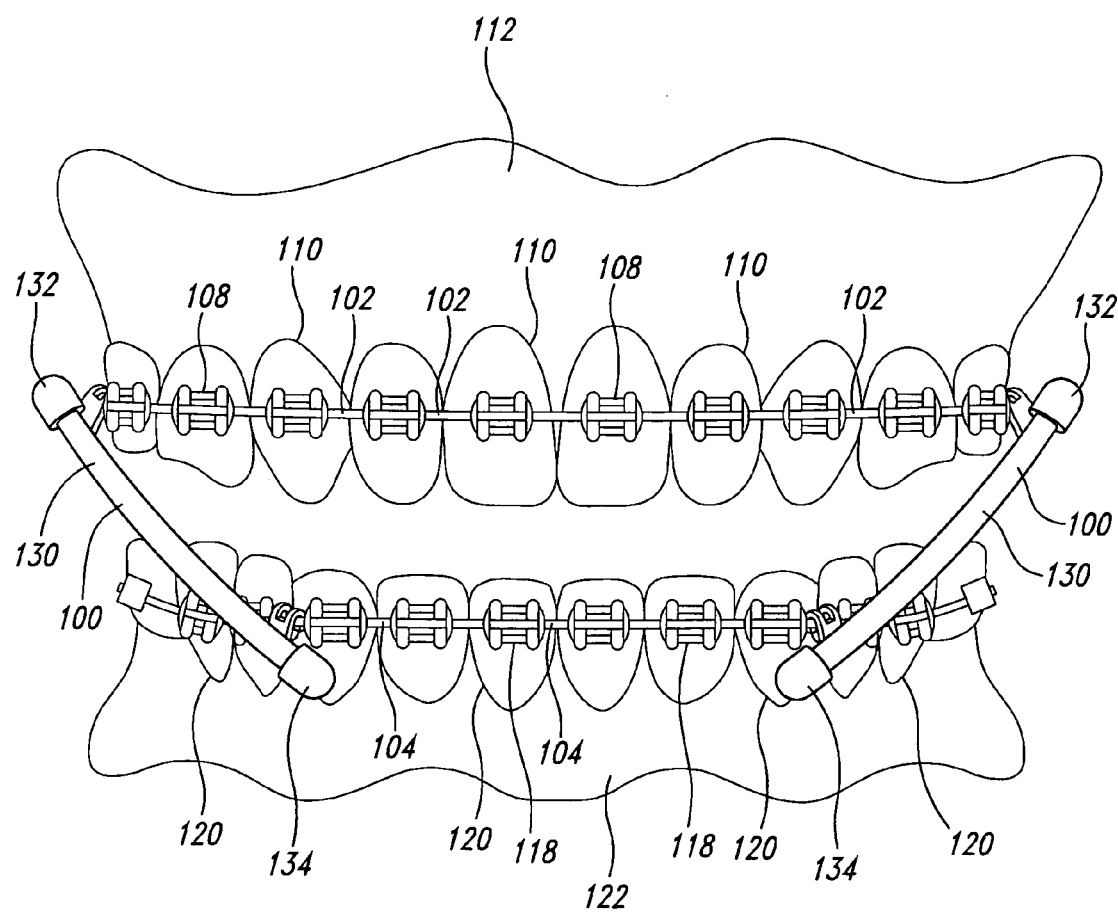

FIG. 2A illustrates the operation of the orthodontic device 100 when the mouth is closed. As seen in FIG. 2A, the curvature in the orthodontic device 100 applies the desired forces to the upper teeth 110 and lower teeth 120, as described above. The orthodontic device may be thought of as "active" when the mouth is in the closed position and the orthodontic device is flexed as shown in FIG. 2A. When the patient mouth is open, the flexible portion of the orthodontic device 100 is relatively straight and thus applies little or no force to the upper teeth 110 and lower teeth 120, as shown in FIG. 2B. When the patient mouth is open, the orthodontic device 100 may be considered in a "passive" stage. When the patient mouth is closed again (see FIG. 2A) the orthodontic device 100 becomes active again.

Figure 3:
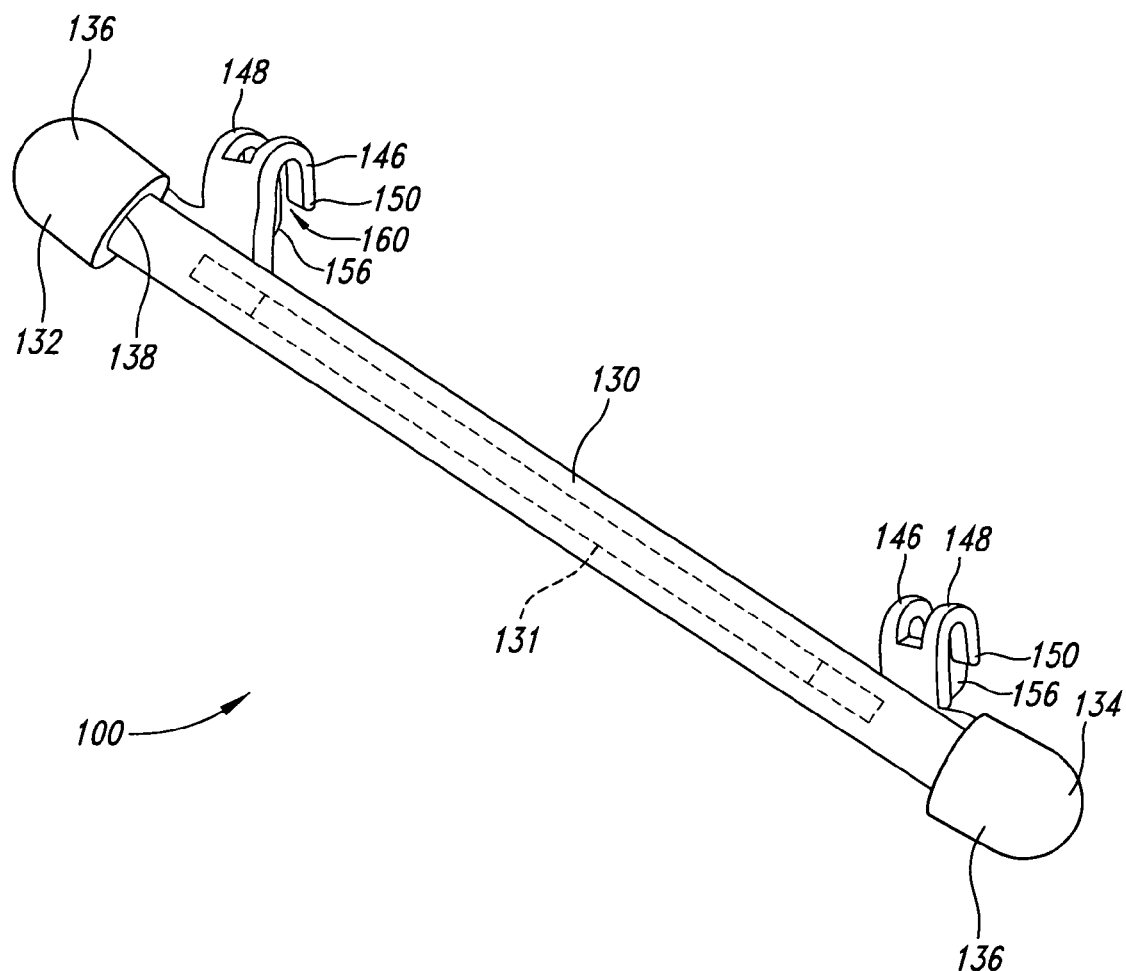
FIG. 3 is a perspective view of the orthodontic device of FIG. 1.

FIG. 3 illustrates the orthodontic device 100 in greater detail. The orthodontic device 100 comprises a flexible central portion 130, which is coupled at its terminal ends to an upper end cap 132 and a lower end cap 134. As will be described in greater detail below, the end caps 132–134 clip directly onto the arch wires and are fully supported thereby. In one embodiment, the central portion 130 is manufactured from polyurethane. In other embodiments, the central portion 130 can be manufactured from any flexible material. Silicone and fiberglass have been used to manufacture the central portion 130. In a preferred embodiment, non-metal materials are used for the central portion 130 to reduce cost and avoid patient discomfort associated with metal components. The flexibility of the central portion 130 is controlled by the selection of manufacturing materials. In an alternative embodiment, a stiffening member 131 may be embedded within the central portion 130 and surrounded thereby. The stiffening member 131 may be manufactured from a different non-metal material than the remaining part of the central portion 130 or manufactured from metal, such as stainless steel, titanium or compound products, such as nickel titanium. The selection of material for the stiffening member 131 is within the skill of the designer producing a product in accordance with the teachings contained herein. The dimensions of the stiffening member 131 as well as the selection of the manufacturing materials may affect the stiffening properties. The stiffening member 131 is embedded in the central portion 130 to provide the desired degree of stiffness of the central portion. Because the stiffening member 131 is embedded within the central portion 130, the patient is not exposed to any metal parts from the orthodontic device 100.

The orthodontic device 100 may be provided in various lengths to accommodate different treatment requirements. The orthodontic devices 100 are also available in a variety of colors in color combinations to accommodate patient preferences. In an exemplary embodiment, the central portion 130 is cylindrical in shape. However, those skilled in the art will appreciate that the central portion 130 may have a circular cross section, oval cross section, square cross section, rectangular cross section, or the like. The orthodontic device 100 is not limited by the specific form used to implement the central portion 130.

Figure 4:
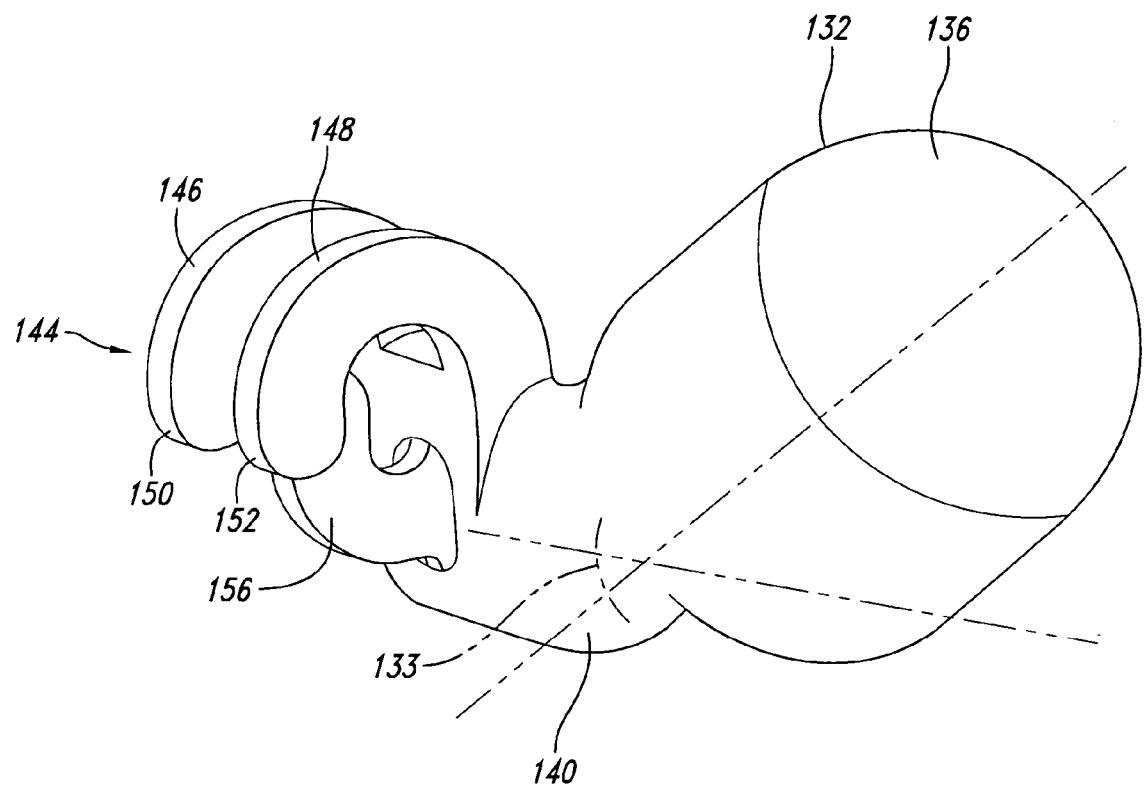
FIG. 4 is a rear perspective view of the upper end cap of the orthodontic device of FIG. 1.

FIGS. 4–9 provide various views of the upper end cap 132. As best seen in FIG. 4, the upper end cap 132 has a rounded terminal portion 136 to improve the comfort level of the patient and to reduce the possibility of damage to the patient's cheek.

Figure 6:
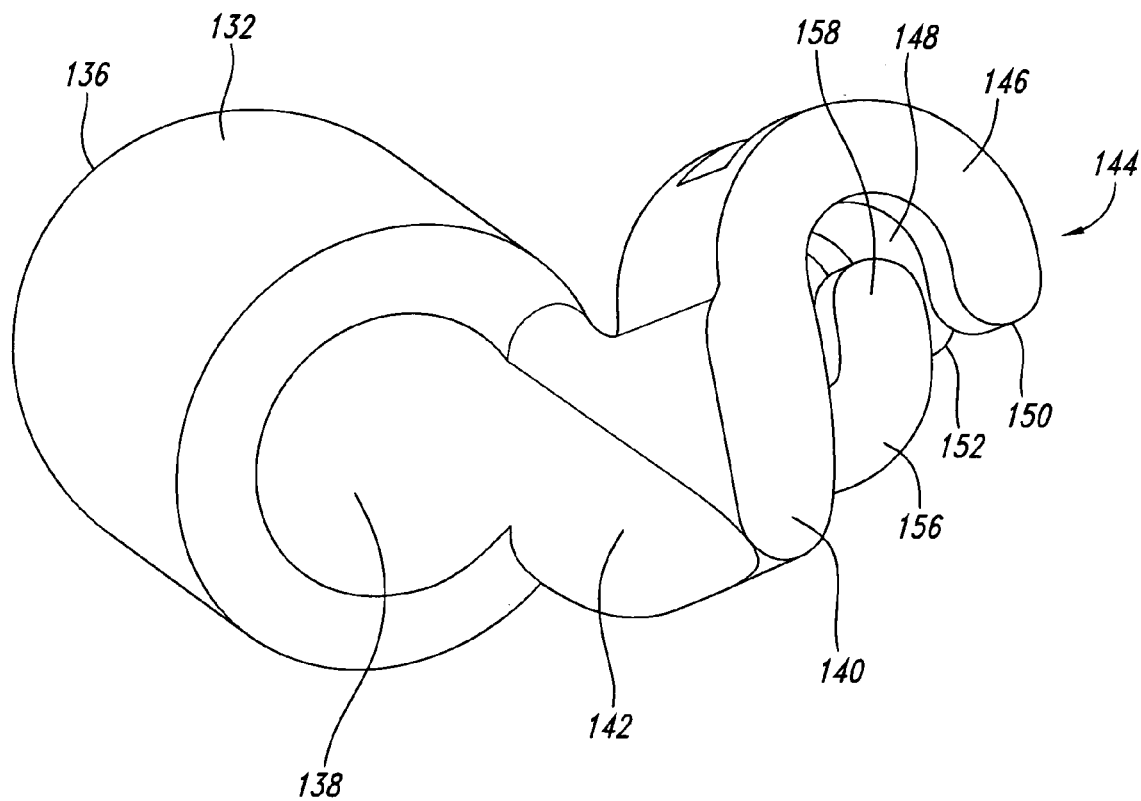
FIG. 6 is a front perspective view of the end cap of FIG. 4.
Figure 7:
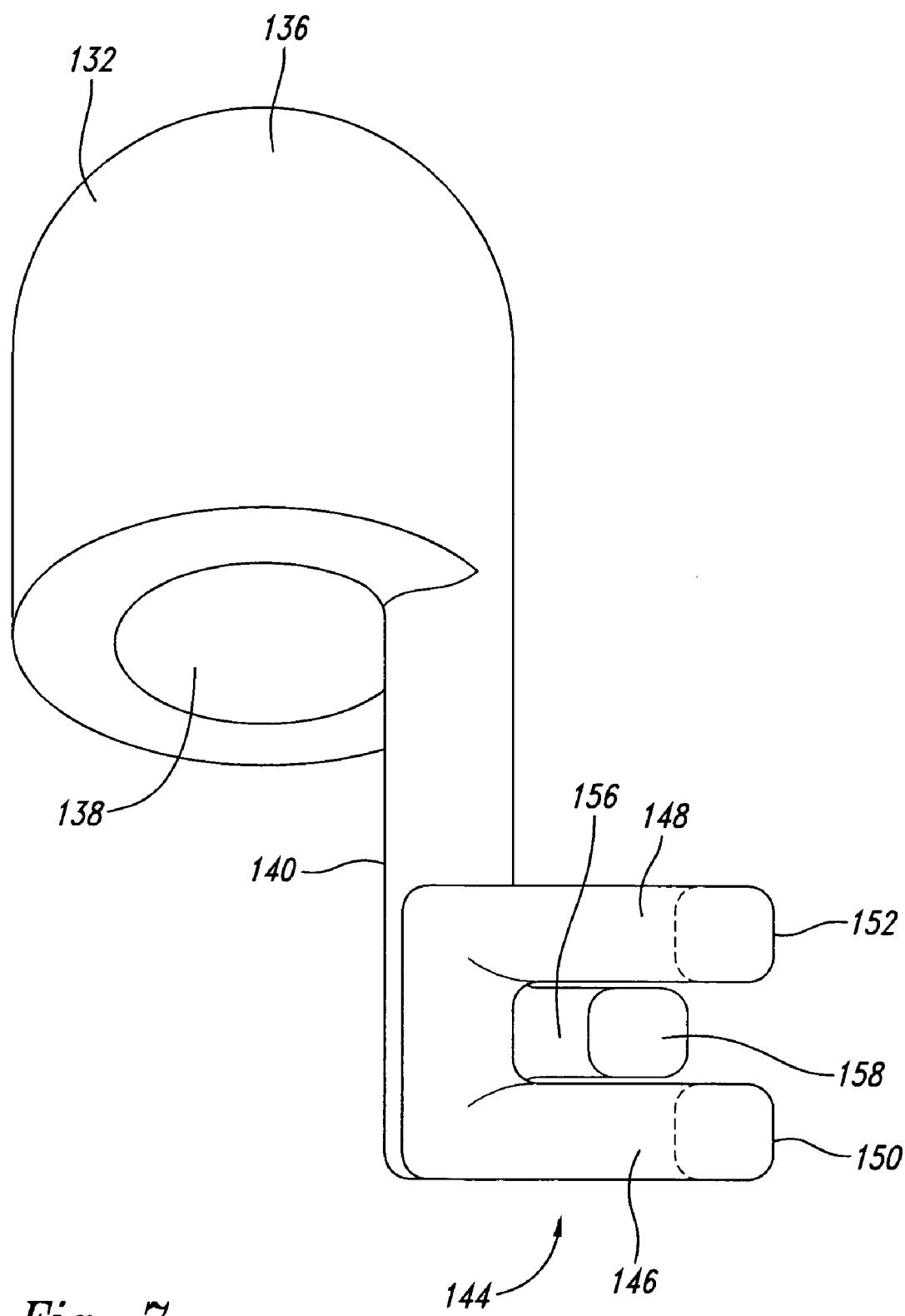
FIG. 7 is a top plan view of the cap of FIG. 4.
Figure 8:
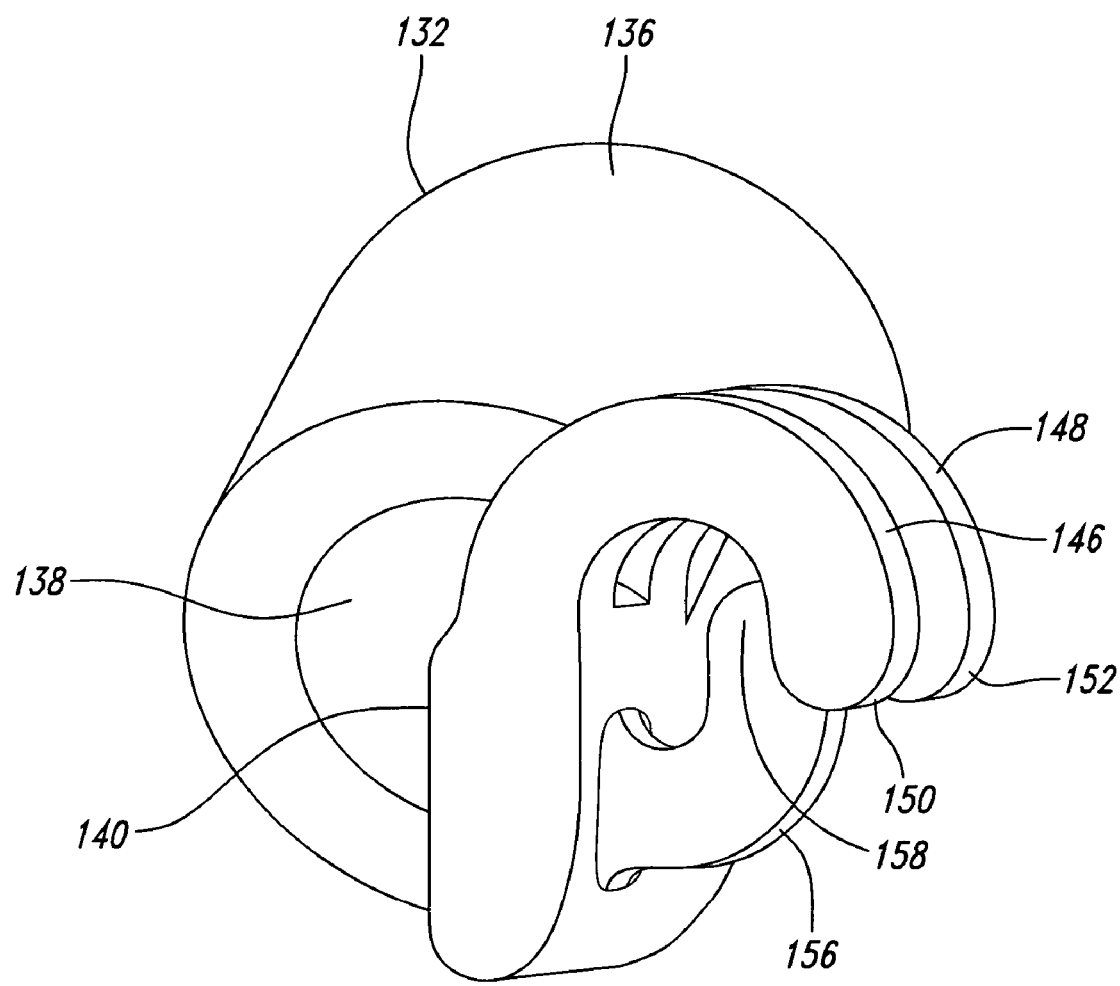
FIG. 8 is a front perspective view illustrating details of the clip mechanism of the cap of FIG. 4.

As best seen in FIG. 6, the upper end cap 132 includes an aperture 138 sized to receive and retain the central portion 130. The central portion 130 may be retained within the aperture 138 using conventional adhesives or mechanical adhesion. In an exemplary embodiment, the central portion 130 is chemically bonded to the upper end cap 132 and retained within the aperture 138 by the chemical bonding process. The central portion 130 may be retained within the aperture 138 using the combination of processes.

As seen in FIGS. 4 and 6, an angled flange 140 extends from the terminal portion 136 of the upper end cap 132. A grooved area 142, shown in FIG. 6, is sized to accommodate the diameter of the central portion 130. The grooved area 142 can be implemented in other shapes to accommodate different shapes of the central portion 130. The flange 140 is angled to provide alignment between the upper end cap 132 and the lower end cap 134. The angled flange 140 allows the upper end cap 132 and lower end cap 134 to be easily clipped onto the upper and lower arch wire 102 and 1.04, respectively.

A clip member 144 is provided at the terminal end of the flange 140 to allow the upper end cap 132 to be clipped to the upper arch wire 102 (see FIG. 1). In an exemplary embodiment, the angled flange 140 is curved to provide an angle 133 (see FIG. 4) in a range from 20° to 40°. Those skilled in the art will appreciate that the angle 133 may be varied from this range to suit particular applications. The clip member 144 comprises first and second curved members 146 and 148, respectively. The first and second curved members 146–148 are coupled to the flange 140 at a first end and curve about a first radius of curvature and terminate at a free end portion 150 and 152, respectively.

As seen in FIG. 4, the first and second curved members 146–148 are spaced apart from each other. A third curved member 156 attaches at a first end to the flange 140 and terminates in a free end portion 158. The third curved member 156 is positioned intermediate to the first and second curved members and extends toward the free end portion with a second radius of curvature different from the radius of curvature of the first and second curved members 146–148. In an exemplary embodiment, the upper end cap 132 utilizes a first curvature of radius for the first and second curved members 146 and 148 that is greater than the second radius of curvature for the intermediate third curved member 156.

Figure 5:
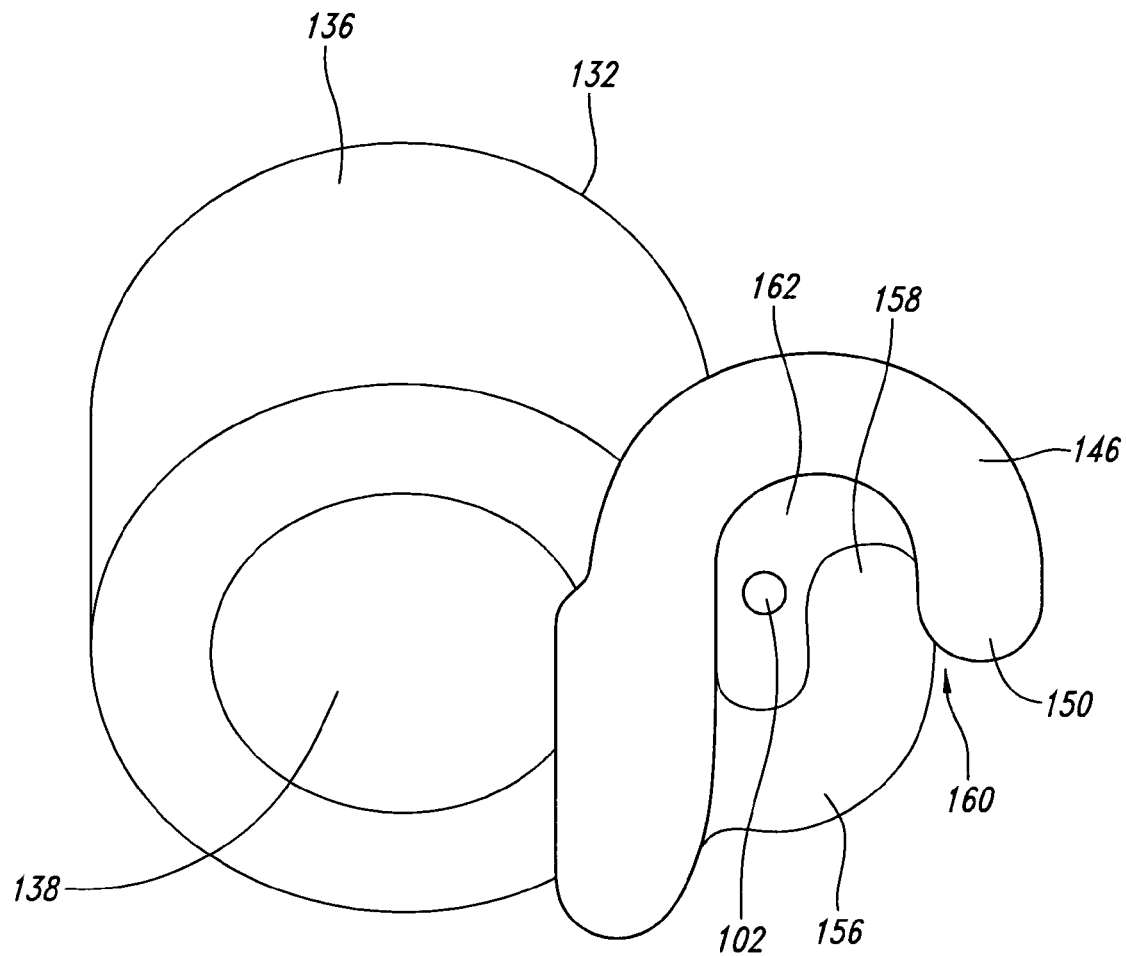
FIG. 5 is a front elevation view of the end cap of FIG. 4.

As best illustrated in FIG. 5, the first and second radii of curvature differ sufficiently so as to create a slight overlap between the free end portions 150 and 152 of the first and second curved members 146–148, respectively, and the free end portion 158 of the third curved member 156. The free end portions 150–152 face the free end portion 158 of the third curved member 156. The opposing free end portions define an entrance 160 where the upper end cap 132 in placed on the upper arch wire 102. In an exemplary embodiment, at least some of the curved members are flexible and can be displaced when the upper end cap 132 is placed on the upper arch wire 102. For example, the first and second curved members 146–148, respectively, may be flexible and can be displaced when the entrance 160 of the upper end cap 132 is placed on the arch wire and pressed into position. This allows the arch wire 102 to move through the entrance 160 and to be captured within a receiver portion 162 defined by the first and second curved members 146–148 and the curved member 156.

In an alternative embodiment, the third curved member 156 is flexible and can be displaced when the entrance 160 is placed over the upper arch wire 102 and clipped into position. And yet another alternative embodiment, all the curved members (i.e., the first and second curved members 146–148 and the third curved member 156) may all exhibit a degree of flexibility to permit displacement when the arch wire 102 passes through the entrance 160 to be captured within the receiver portion 162, as illustrated in FIG. 5.

In yet another alternative embodiment, the radius of curvature between the first and second curved members 146–148 and the third curved member 156 is sufficiently great such that the entrance 160 forms a gap between the free end portions of the respective curved members. The radii curvature are selected such that the gap in the entrance 160 is slightly smaller than the size of the upper arch wire 102 (see FIG. 1). Those skilled in the art will appreciate that the arch wire (e.g., the upper arch wire 102) may be circular in shape. In this event, the gap in the entrance 160 may be slightly smaller than the diameter of the selected arch wire (i.e., the upper arch wire 102 of FIG. 1). For example, a typical round arch wire may have a diameter ranging from 0.012" to 0.022". In an exemplary embodiment, the gap in the entrance 160 may be set to approximately 0.020". In some applications, the arch wire 102 may be rectangular in shape. For example, a typical dimension of rectangular arch wire is 0.022" by 0.028". In this implementation, the gap in the entrance 160 may be slightly smaller than the size of the rectangular arch wire 102.

The receiver portion 162 receives and slidably retains the arch wire (i.e., the arch wire 102 of FIG. 1). Thus, the orthodontist clips the upper end cap 132 by positioning the entrance 160 over the arch wire 102 and pressing the upper end cap 132 into position with a downward movement. Once in position, the arch wire 102 is retained within the receiver portion 162 and the upper end cap 132 slides freely thereon. The sliding of the upper end cap 132 is restricted by the brackets 108.

Those skilled in the art will appreciate that the upper end cap 132 could be implemented using only the first and third curved members 146 and 156, respectively, or using only the second and third curved members 148 and 156. However, the use of both the first and second curved members 146–148 helps maintain the desired alignment of the orthodontic device 100. The flange 140 is angled so that the aperture 138 points downward in the direction of the second end cap 134 when the clip member 144 has been installed on the upper arch wire 102.

FIGS. 10–15 provide details of the lower end cap 134. Most features of the lower end cap 134 are symmetrical with the features of the upper end cap 132 and need not be described in greater detail. However, in an exemplary embodiment, the radius of curvature of the first and second curved members 146–148 is less than the radius of curvature of the intermediate third curved member 156. Thus, the free end portion 158 of the lower end cap 134 extends beyond the free end portions 150–152 of the first and second curved members 146–148, respectively. This arrangement allows greater ease in clipping the lower end cap 134 onto the lower arch wire 102 (see FIG. 1) with an upward movement of the lower end cap. However, those skilled in the art will appreciate that the lower end cap could be implemented with the same radii of curvature as the upper end cap 132. Alternatively, the upper end cap 132 may be implemented with the configuration of curved members shown in FIGS. 9–15 for the lower end cap 134.

It should also be noted that the flange 140 on the lower end clip 134 curves in the opposite direction as the flange 140 of the upper end cap 132. The flange 140 on the lower end cap 134 is angled such that the aperture 138 (see FIG. 12) points in the direction of the upper end cap 132 when the clip member 144 of the lower end cap 134 is installed on the lower arch wire 102.

The configuration of the clip member 144 of the upper end cap 132 is designed to accommodate the installation of the upper end cap on the upper arch wire 102 in a downward motion. That is, the orthodontist positions the upper end cap 132 of the orthodontic device 100 above the desired location on the upper arch wire 102 (see FIG. 1). As best seen in FIG. 5, the curved surface of the third curved member 156 serves to guide the orthodontic device 100 such that the upper arch wire 102 is guided to the entrance 160.

Figure 11:
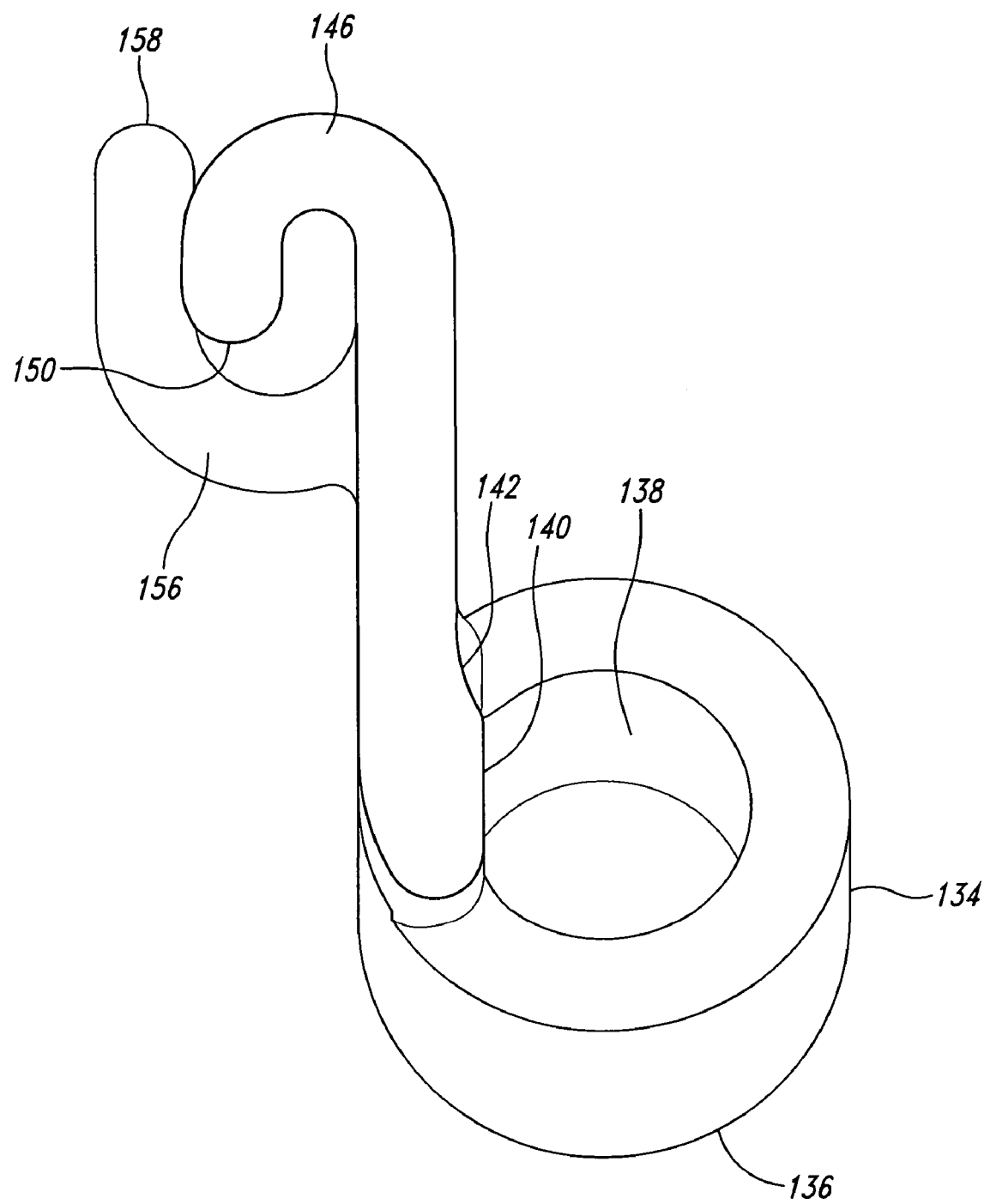
FIG. 11 is a front elevation view of the end cap of FIG. 10.
Figure 12:
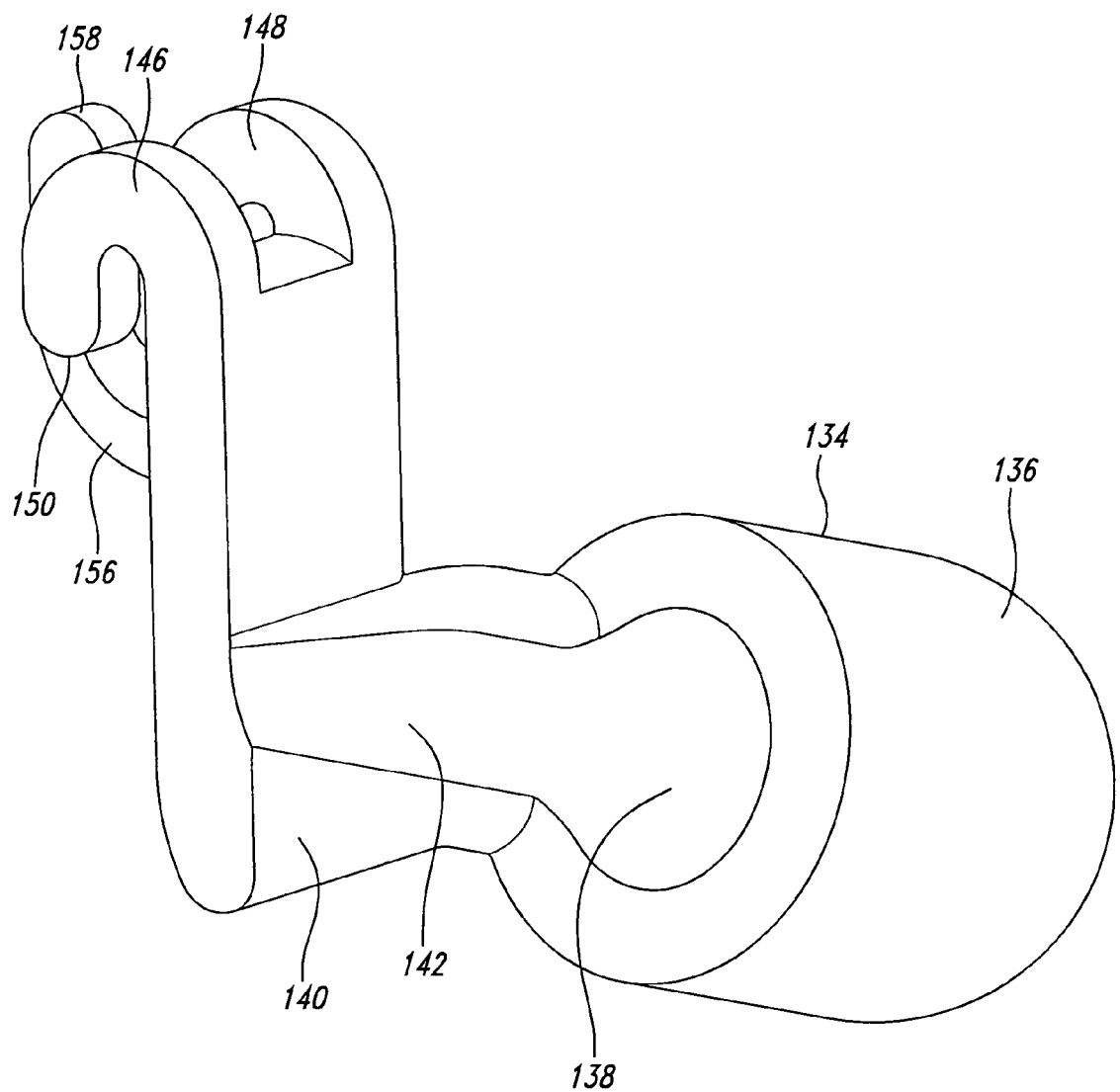
FIG. 12 is a front perspective view of the cap of FIG. 10.
Figure 13:
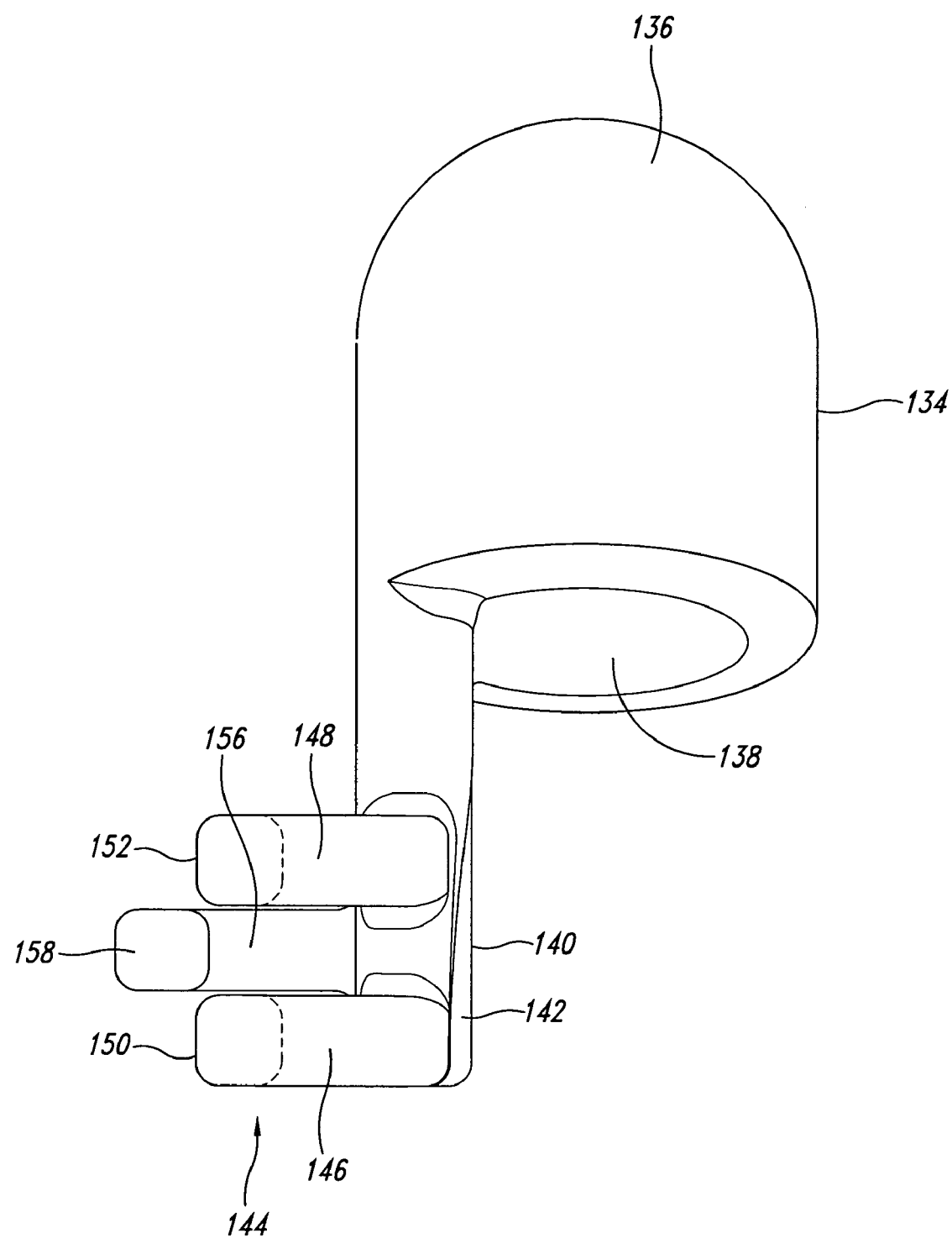
FIG. 13 is a top plan view of the cap of FIG. 10.
Figure 14:
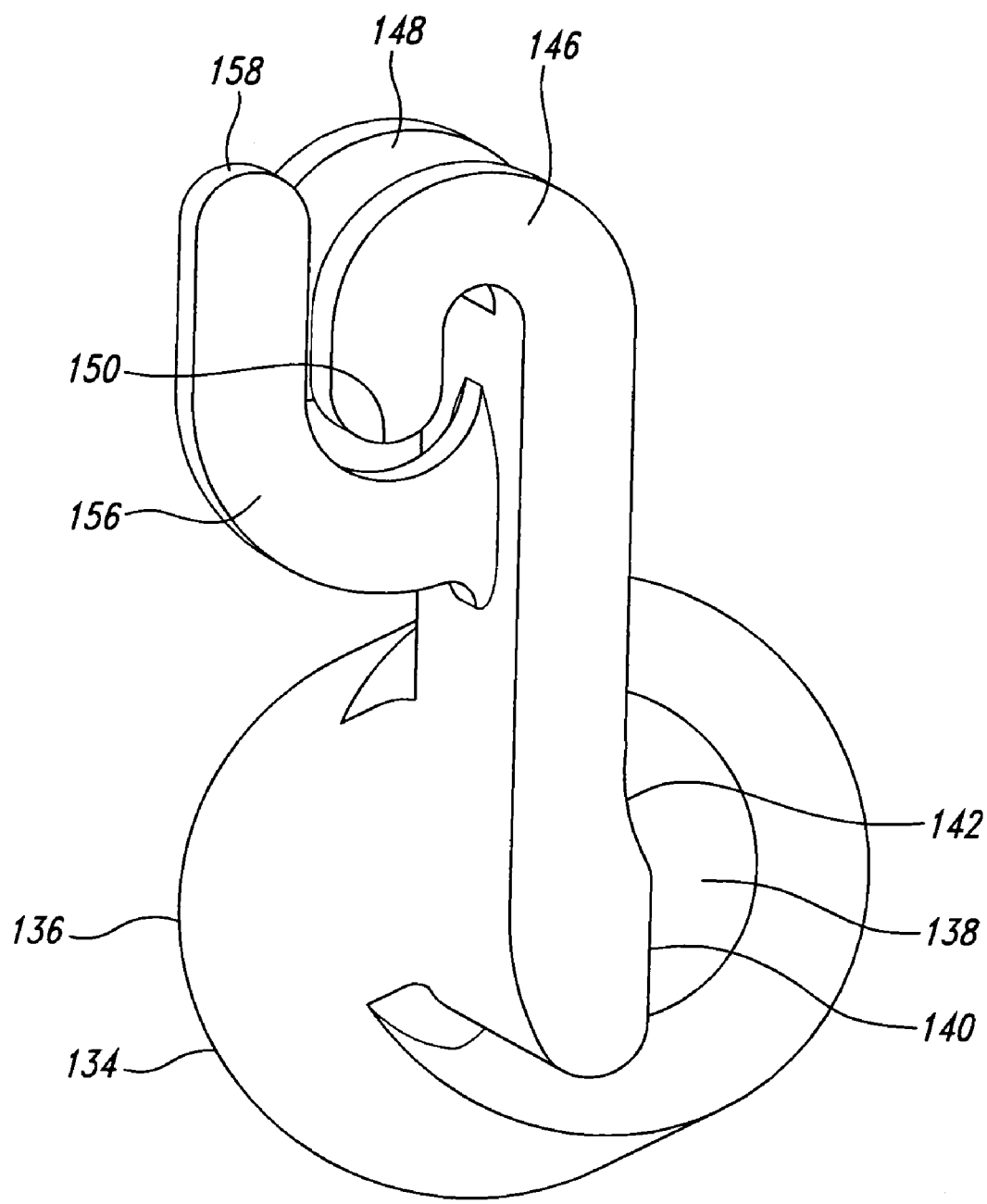
FIG. 14 is a front perspective view illustrating details of the clip mechanism of the cap of FIG. 10.

Similarly, the clip member 144 of the lower end cap 132 is designed to accommodate the installation of the lower end cap on the lower arch wire 104 in an upward movement. That is, the orthodontist positions the lower end cap 134 of the orthodontic device 100 below the desired location on the lower arch wire 104. As best seen in FIG. 11, the curved surfaces of the first and second curved members 146–148 serve to guide the orthodontic device such that the lower arch wire 104 is guided to the entrance 160.

As the orthodontist moves the lower end cap 134 in an upward direction, the lower arch wire 104 moves through the entrance 160 and is held in place within the receiver portion 162 of the lower end cap. The receiver portion 162 receives and slidably retains the lower end cap 134 on the lower arch wire 104. Once in position, the lower arch wire 104 is contained within the receiver portion 162 and slides freely thereon. The sliding of the lower end cap 134 is restricted by the brackets 118.

Figure 9:
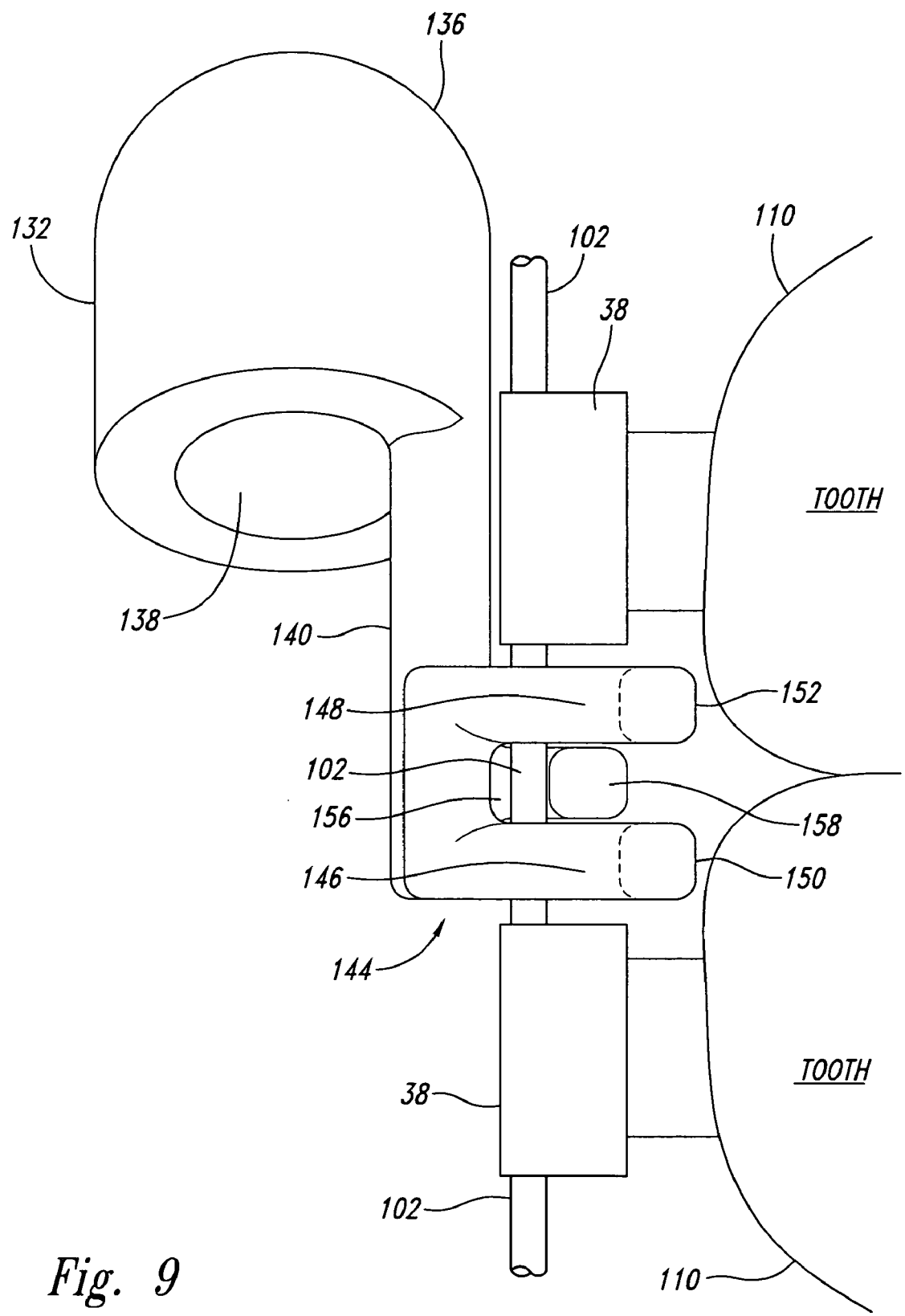
FIG. 9 is a top plan view of the cap of FIG. 4 illustrating its installation on orthodontic wires.
Figure 10:
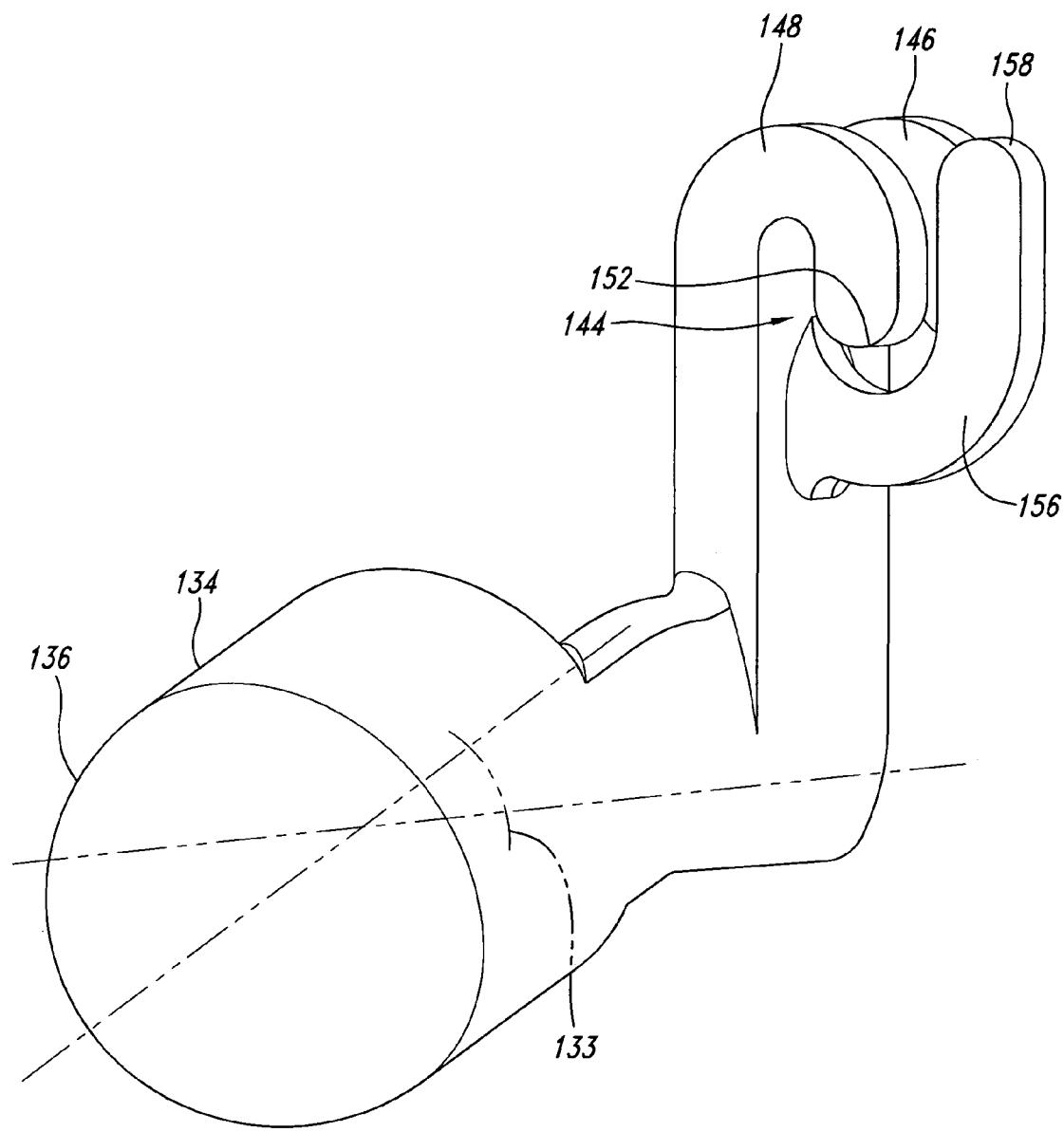
FIG. 10 is a rear perspective view of the lower cap of the orthodontic device of FIG. 3.
Figure 15:
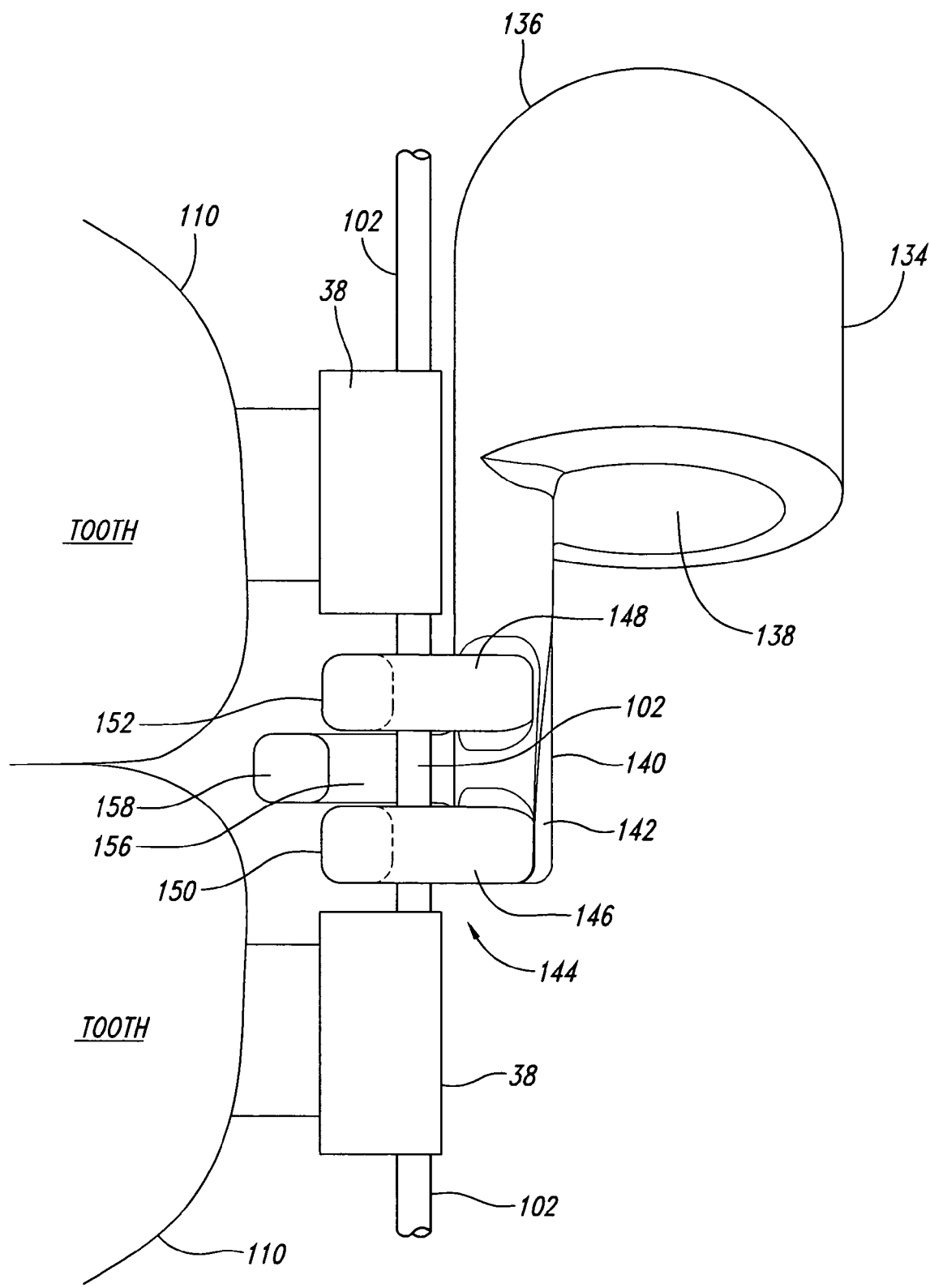
FIG. 15 is a top plan view of the cap of FIG. 10 illustrating its installation on orthodontic wires.

FIG. 9 illustrates the operation of the brackets 108 in limiting the lateral sliding movement of the upper end cap 132 along the upper arch wire 102. The upper arch wire 102 is smaller in size than the receiver portion 162 thus permitting the upper end cap 132 to slide freely along the upper arch wire. Because of the relatively short distance between the brackets 108, the upper end cap 132 can only slide a limited distance on the upper arch wire 102 before encountering the brackets 108. Similarly, FIG. 15 illustrates the operation of the brackets 118 in limiting lateral sliding movement of the lower end cap 134 along the lower arch wire 104. Again, the lower arch wire 104 is smaller than the receiver portion 162 of the lower end cap 134 thus allowing the lower end cap to slide freely on the lower arch wire. However, the short distance between the brackets 118 limits the sliding movement of the lower bracket 134. It should be noted that not all elements in FIGS. 9 and 15 are drawn to scale so that the installation and operation of the orthodontic device 100 may be readily understood.

Those skilled in the art will appreciate that the curved features of the clip member 144 are designed to facilitate installation of the upper and lower end caps 132–134, respectively, as well as to minimize discomfort to the patient. However, those skilled in the art will appreciate that the clip member 144 could be implement in a variety of shapes. Accordingly, the orthodontic device 100 is not limited to specific shapes in the clip member 144. For example, the clip member 144 could be implemented with angled members rather than the continuously curved members shown in the drawings. The angled members could be beveled to minimize discomfort to the patient and still have dimensions so as to provide the gap 160 having a dimension approximately the size of the arch wire. Thus, the end caps would still have the beneficial feature of clipping directly onto the arch wire and being fully supported thereon.

As best seen in FIG. 2A, the orthodontic device 100 of FIG. 3 is positioned with the upper end cap 132 clipped on the upper arch wire 102 while the lower end cap 134 is clipped on the lower arch wire 104. In this embodiment, the central portion 130 assumes a slightly curved configuration, as illustrated in FIG. 2. The central portion 130 bows slightly in a substantially horizontal plane defined by the upper and lower end caps 132–134. This orientation of the orthodontic device 100 is well known in the art.

Figure 16:
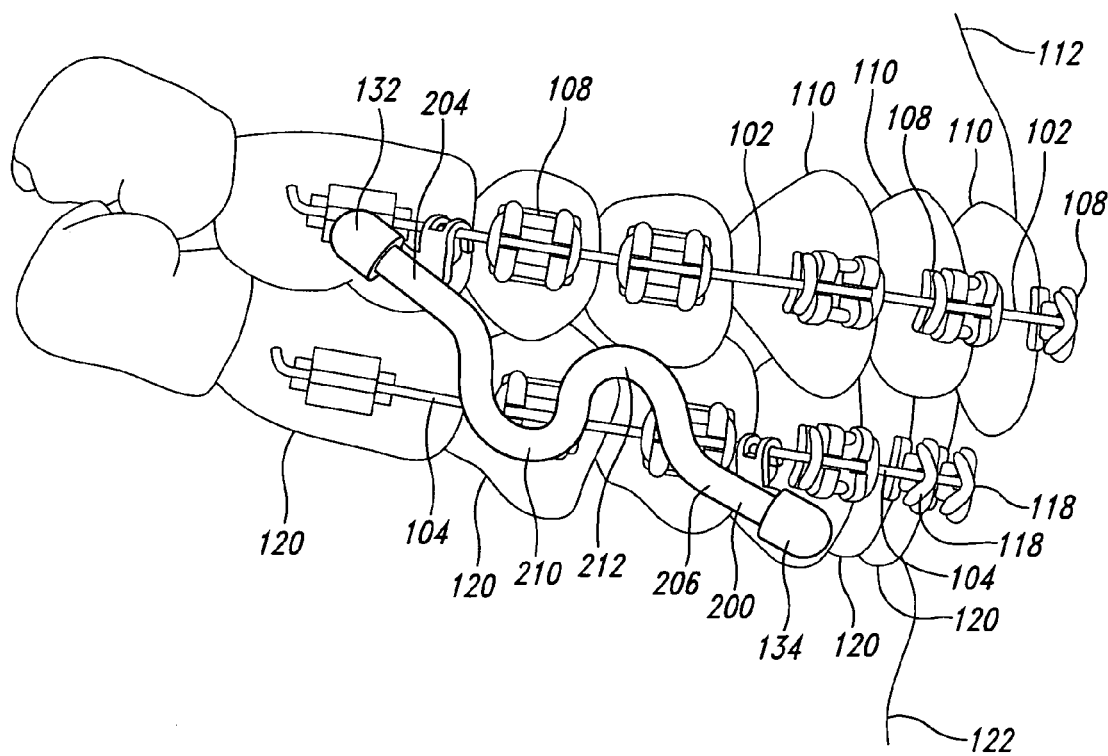
FIG. 16 is a right side view of teeth with braces utilizing an alternative embodiment of the orthodontic device attached to orthodontic wires.
Figure 17:
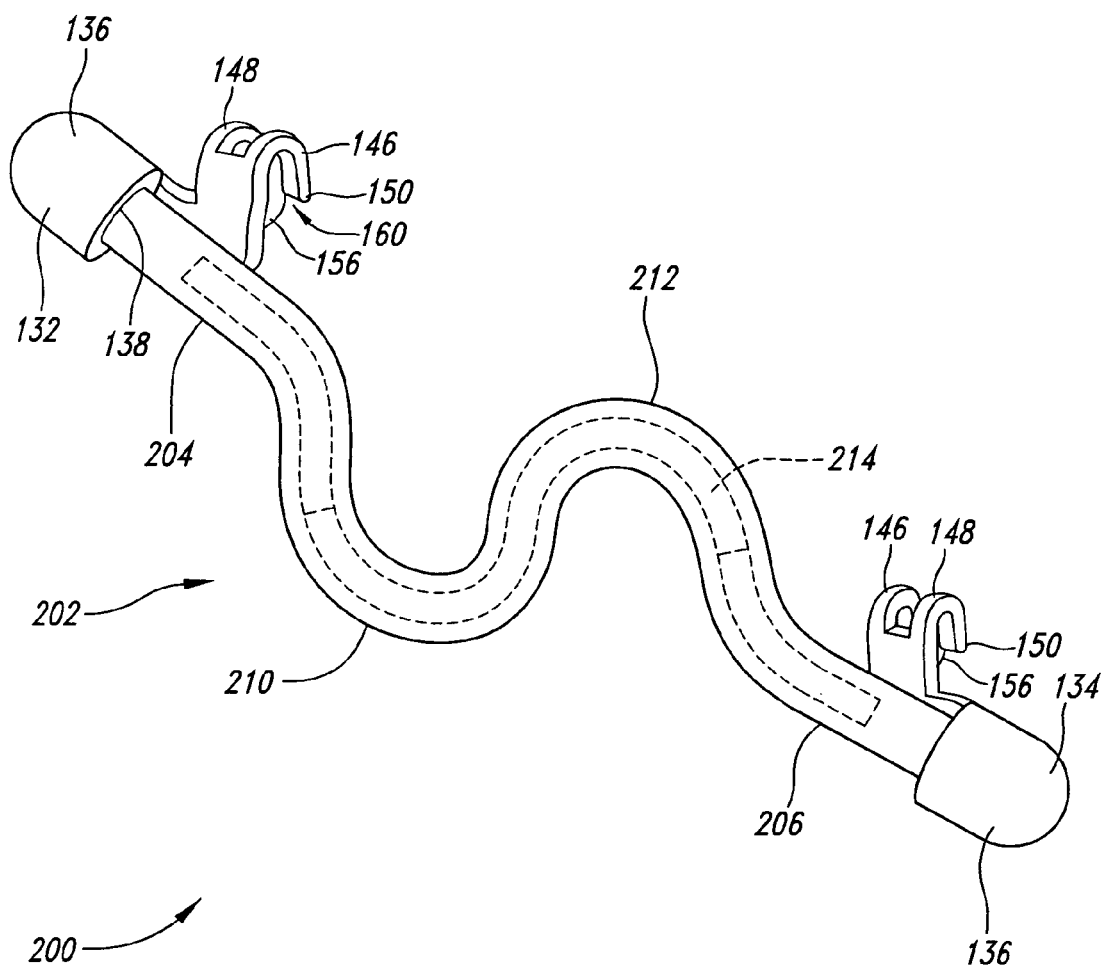
FIG. 17 is a perspective view of the orthodontic device of FIG. 16.

In an alternative configuration, an orthodontic device 200 is provided in a curved configuration, as illustrated in FIGS. 16–17. The upper end cap 132 and lower end cap 134 are identical to that described above with respect to the orthodontic device 100. However, the orthodontic device 200 has a curved central portion 202. As illustrated in FIG. 17, the central portion 202 has linear straight end sections 204–206. The straight end section 204 points toward the upper end cap 132 and the lower end cap 134. A terminal portion of the straight end section 204 is positioned within the aperture 138 (see FIG. 6) of the upper end cap 132. Similarly, the straight end section 206 points generally toward the upper end cap 132 and the lower end cap 134. A terminal portion of the straight end section 206 fits within the aperture 138 (see FIG. 12) of the lower end cap 134. Intermediate the straight end sections 204–206, the central portion 202 has a bowed section 210 adjacent the straight end section 204. Similarly, a bowed section 212 is adjacent to the straight end section 206 and adjoins the bowed section 210. As illustrated in FIG. 17, the bowed section 210 is bowed in a first direction while the bowed section 212 is bowed in a second direction different from the first direction. In an exemplary embodiment, the bowed sections 210 and 212 are bowed in opposite directions and are substantially co-planar.

FIG. 16 illustrates the orthodontic device 200 as installed in a typical implementation. It should be noted that the orthodontic device 200 is designed for displacement in a substantially vertical plane. This orientation minimizes intrusion into the patient's mouth and decreases the level of discomfort experienced by the patient.

In an exemplary embodiment, the central portion 202 of the orthodontic device 200 is manufactured with polyurethane plastic. As with the central portion 130, the central portion 202 may be manufactured from other flexible material. In a preferred embodiment, the central portion 202 is manufactured from non-metal materials. In effect, the central portion 202 is a plastic spring. In an alternative embodiment, the central portion 202 may contain an internal stiffening member 214. The stiffening member 214 may have the same characteristics as the stiffening member 131 discussed above with respect to FIG. 3. In the embodiment illustrated in FIG. 17, the optional stiffening member 214 is completely embedded within the central portion 202 of the orthodontic device 200 and is positioned in the bowed sections 210 and 212. In an alternative embodiment, the metal stiffening member 214 may extend throughout the length of the central portion 202.

At rest, the central portion 202 experiences no displacement and no stress. That is, no tension has been applied to the central portion 202. Under tension, the straight end sections 204–206 are moved closer together (i.e. either one or both of the straight end sections move toward each other). The greatest stress concentrations are experienced in the bowed sections 210 and 212 when the central portion 202 is under tension.

Thus, the orthodontic devices described herein clip easily onto the arch wires and are fully supported by the arch wires. This approach is made possible by the low-cost plastic end caps and clip members. The orthodontic devices are provided in a variety of lengths and in a variety of stiffness ratings to accommodate various therapeutical conditions. In addition, the orthodontic devices may be provided in a variety of colors for selection by the patient. The use of an all plastic orthodontic device minimizes cost and simplifies production. In addition, the rounded surfaces provided by the non-metal orthodontic devices minimizes discomfort to the patient and reduces the possibility of injury to the cheeks of the patient.

The figures showing the orthodontic devices (i.e. the orthodontic device 100 and the orthodontic device 200) have been shown for installation on the right side of the patient's mouth. Those skilled in the art will appreciate that mirror image orthodontic devices are available for installation on the left side of the patient's mouth. Because the devices are operationally equivalent, the left side mirror image devices are not shown in the drawings and need not be explained in greater detail herein.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

The invention claimed is:

1. An orthodontic device to clip onto orthodontic wire, comprising:
    an elongated flexible central portion having first and second end portions;
    a first clip fixedly coupled to the first end portion, the first clip having a clip member with a gap portion to clip onto the orthodontic wire without the removal of the orthodontic wire from an orthodontic bracket; and
    a second clip fixedly coupled to the second end portion, the second clip having a clip member with a gap portion to clip onto the orthodontic wire without the removal of the orthodontic wire from an orthodontic bracket.

2. The device of claim 1 wherein the clip members have a receiver portion sized to receive and slideably retain the orthodontic wire.

3. The device of claim 2 for use with orthodontic wire coupled to braces wherein the clip members slide on the orthodontic wire to a point wherein the clip members encounter an orthodontic bracket.

4. The device of claim 1 wherein the central portion is manufactured of polyurethane.

5. The device of claim 1 wherein the first and second clips are chemically bonded to the central portion.

6. The device of claim 1 wherein the first and second clips are bonded to the central portion with an adhesive.

7. The device of claim 1 wherein the first and second clips and the central portion contain no metal.

8. The device of claim 1, further comprising a stiffening member embedded in the central portion.

9. The device of claim 8 wherein the stiffening member embedded in the central portion is a metal stiffening member.

10. The device of claim 1 wherein the central portion comprises a first bowed section bowed in a first direction and a second bowed section bowed in a second direction different from the first direction.

11. The device of claim 10 wherein the first and second bowed sections are substantially co-planar.

12. The device of claim 10 wherein the central portion comprises a first linear section coupled to the first bowed section and extending toward the first clip and a second linear section coupled to the second bowed section and extending toward the second clip.

13. The device of claim 1 wherein the first and second clip members each comprise:
    first and second spaced apart arcuate members coupled to and extending from each of the first and second clips, each of the first and second arcuate members having a first end portion coupled to the clip and a second free end portion; and
    an intermediate arcuate member positioned intermediate the first and second arcuate members, the intermediate arcuate member coupled to and extending from each of the first and second clips, the intermediate arcuate member having a first end portion coupled to the clip and a second free end portion, the first and second arcuate members and the intermediate arcuate member defining a receiver portion.

14. The device of claim 13 wherein the receiver portion is sized to receive and retain the orthodontic wire.

15. The device of claim 13 wherein the first and second members have a first radius of curvature and the intermediate member has a second radius of curvature less than the first radius of curvature.

16. The device of claim 13 wherein the first and second members have a first radius of curvature and the intermediate member has a second radius of curvature greater than the first radius of curvature.

17. The device of claim 13 wherein the first and second members have a first radius of curvature and the intermediate member has a second radius of curvature is sufficiently different from the first radius of curvature to form a gap between the free end portions of the first and second members and the free end portion of the intermediate member.

18. The device of claim 13 wherein at least a portion of the arcuate members are flexible to permit the insertion of the orthodontic wire into the receiver portion.

19. A clip for attaching an orthodontic device to an orthodontic wire, comprising:
    first and second spaced apart arcuate members coupled to and extending from the clip, each of the first and second arcuate members having a first end portion coupled to the clip and a second free end portion; and
    an intermediate arcuate member positioned intermediate the first and second arcuate members, the intermediate arcuate member coupled to and extending from the clip, the intermediate arcuate member having a first end portion coupled to the clip and a second free end portion, the first and second arcuate members and the intermediate arcuate member defining a receiver portion.

20. The device of claim 19 wherein the receiver portion is sized to receive and retain the orthodontic wire.

21. The device of claim 19 wherein the first and second members have a first radius of curvature and the intermediate member has a second radius of curvature is sufficiently different from the first radius of curvature to form a gap between the free end portions of the first and second members and the free end portion of the intermediate member.

22. The device of claim 19 wherein at least a portion of the arcuate members are flexible to permit the insertion of the orthodontic wire into the receiver portion.

23. An orthodontic device to clip an orthodontic force module onto orthodontic wire, comprising:
a cap portion having an aperture sized to receive a retain the orthodontic force module; and
a clip extending from the cap portion, the clip clipping directly onto the orthodontic wire without removal of the orthodontic wire from an orthodontic bracket wherein the cap portion is retained in position by the clip clipped onto the orthodontic wire.

24. The device of claim 23 wherein the clip comprises first and second members extending from the cap portion, the first and second members each having a first end portion coupled to the cap portion and a second free end portion.

25. The device of claim 24 wherein the free end portion of the first member and the free end portion of the second member are opposing.

26. The device of claim 24, further comprising a third member extending from the cap portion with a first end portion coupled to the cap portion and a second free end portion, the third member being spaced apart from the first member with the second member intermediate the first and third members.

27. The device of claim 23 wherein the clip comprises first and second curved members extending from the cap portion, the first curved member having a first end portion coupled to the cap portion and a second free end portion and a first radius of curvature, the second curved member having a first end portion coupled to the cap portion and a second free end portion and a second radius of curvature different from the first radius of curvature.

28. The device of claim 27 wherein the first radius of curvature is sufficiently different from the second radius of curvature to form a gap between the free end portion of the first curved member and the free end portion of second curved member.

29. The device of claim 28 wherein the gap between the free end portions of the first and second curved members is approximately the size of the orthodontic wire.

30. The device of claim 23 wherein the clip comprises first and second opposing members that define a receiver portion sized to receive and retain the orthodontic wire.

31. The device of claim 30 wherein at least a portion of the first and second members are flexible to permit the insertion of the orthodontic wire into the receiver portion.

32. A method for orthodontic treatment with braces comprising:
selecting an orthodontic force module;
clipping a first end of the orthodontic force module onto an orthodontic wire at a first location without having to remove the wire from an orthodontic bracket; and
clipping a second end of the orthodontic force module onto an orthodontic wire at a second location without having to remove the wire from an orthodontic bracket wherein the first and second ends of the orthodontic force module are clipped onto the orthodontic wire at the first and second locations, respectively, and are attached to and fully supported by the orthodontic wire at the first and second locations.

33. The method of claim 32 wherein selecting the orthodontic force module comprises selecting a force module having a predetermined length such that the force module applies a force between first and second ends of the force module when clipped to the orthodontic wire and a patient mouth is closed.

34. The method of claim 33 wherein the predetermined length is selected such that the force module applies a decreased force between first and second ends of the force module when clipped to the orthodontic wire and a patient mouth is open.

35. The method of claim 32 for use with the first end of the orthodontic force module having a first member extending from the cap portion to terminate in a free end portion, and a second member extending from the cap portion to terminate in a second free end portion wherein clipping the first end to the orthodontic wire comprises placing the free end portions of the first and second members on opposite sides of the orthodontic wire to thereby clip the first end to the orthodontic wire.

36. The method of claim 35 wherein the free end portions of the first and second members are opposing and clipping the first end to the orthodontic wire comprises placing the opposing free end portions of the first and second members on opposite sides of the orthodontic wire to thereby clip the first end to the orthodontic wire.

37. The method of claim 35 wherein the first member is flexible and clipping the first end to the orthodontic wire comprises using the orthodontic wire to flex the first member to thereby clip the first end to the orthodontic wire.

38. The method of claim 32 for use with the first end of the orthodontic force module having a first and second spaced apart members each extending from the cap portion to terminate in first and second free end portions, respectively, and a third member intermediate the first and second members and extending from the cap portion to terminate in a third free end portion wherein clipping the first end to the orthodontic wire comprises placing the free end portions of the first and second members and the free end portion of the third member on opposite sides of the orthodontic wire to thereby clip the first end to the orthodontic wire.

39. The method of claim 38 wherein the free end portions of the first and second members are opposing the free end portion of the third member and clipping the first end to the orthodontic wire comprises placing the opposing free end portions of the first and second members on opposite sides of the orthodontic wire to thereby clip the first end to the orthodontic wire.

40. The method of claim 38 wherein at least one of the first, second, and third members is flexible and clipping the first end to the orthodontic wire comprises using the orthodontic wire to flex the flexible member to thereby clip the first end to the orthodontic wire.

41. The method of claim 38 wherein the free end portion of the first and second members and the free end portion of third member are positioned to form a gap there between and clipping the first end to the orthodontic wire comprises positioning the gap on opposite sides of the orthodontic wire to thereby clip the first end to the orthodontic wire.

* * * * *